United States Patent
Ottenhoff et al.

(10) Patent No.: US 6,251,126 B1
(45) Date of Patent: Jun. 26, 2001

(54) METHOD AND APPARATUS FOR SYNCHRONIZED TREATMENT OF OBSTRUCTIVE SLEEP APNEA

(75) Inventors: Frans A. M. Ottenhoff; Koen J. Michels, both of Maastricht (NL)

(73) Assignee: Medtronic INC, Minneapolis, MN (US)

( * ) Notice: Subject to any disclaimer, the term of this patent is extended or adjusted under 35 U.S.C. 154(b) by 0 days.

(21) Appl. No.: 09/411,845

(22) Filed: Oct. 4, 1999

Related U.S. Application Data (63) Continuation of application No. 09/064,729, filed on Apr. 23, 1998, now abandoned.

(51) Int. Cl.[7] .................................................. A61N 1/00
(52) U.S. Cl. ............................................................. 607/42
(58) Field of Search ................................ 607/42, 72, 44

(56) References Cited

U.S. PATENT DOCUMENTS

| | | | |
|---|---|---|---|
| 4,830,008 | 5/1989 | Meer | 128/421 |
| 5,335,657 | 8/1994 | Terry, Jr. et al. | 607/45 |
| 5,344,438 | 9/1994 | Testerman et al. | 607/118 |
| 5,549,655 | 8/1996 | Erickson | 607/42 |
| 5,591,216 | 1/1997 | Testerman et al. | 607/42 |

*Primary Examiner*—Scott M. Getzow
(74) *Attorney, Agent, or Firm*—Thomas F. Woods; Michael J. Jaro; Harold Patton (57) ABSTRACT

A method and apparatus for synchronized treatment of obstructive sleep apnea. In one embodiment such stimulation is provided by an implantable pulse generator, the implantable pulse generator having a stimulation stage to output stimulation pulses to a body structure, a sensing stage to sense the respiratory effort of a patient, and a controller, to coordinate, and preferably to synchronize, the output stimulation pulses with the sensed respiratory effort. The respiratory effort of a patient is sensed through the use of two electrodes disposed such that the diaphragm is positioned between, and the high frequency current is injected from one electrode to the other and the corresponding impedance is measured, the corresponding impedance thus being a function of the diaphragm position, itself indicating the respiratory effort of the patient. In such a manner the present invention permits the delivery of stimulation to be precisely controlled by the actual respiratory effort of the patient.

16 Claims, 6 Drawing Sheets

METHOD AND APPARATUS FOR SYNCHRONIZED TREATMENT OF OBSTRUCTIVE SLEEP APNEA

This application is a continuation of application Ser. No. 09/064,729, filed Apr. 23, 1998, now abandoned.

FIELD OF THE INVENTION

The present invention concerns the field of medical electrical stimulation and, in particular, concerns the method and apparatus for synchronized treatment of obstructive sleep apnea.

BACKGROUND OF THE INVENTION

Obstructive Sleep Apnea (OSA) is a common disorder in western society, affecting between approximately 4 to 9% of the general population over the age of 40. It is a condition where the upper airway may be occasionally obstructed, either partially or completely, during sleep. Such obstructions may result in an interruption of sleep or at the least diminished quality of sleep. The primary clinical symptom is daytime hypersomnolence. This condition can significantly interfere with a patient's ability to function normally. Long-term medical consequences of chronic, untreated OSA may include pulmonary and systemic hypertension, cardiac arrhythmias, increased likelihood of myocardial infarction and ultimately, cardiac failure.

To treat obstructive sleep apnea, upper airway collapse can be relieved in many ways. One approach is to bypass the upper airway so that even if the airway collapses, there is an alternative route for air to flow. Such a bypass is accomplished through a tracheostomy procedure. This of course is highly invasive, costly and not currently favored. Another approach is to reverse the upper airway collapse. Many treatments may be used to reverse the upper airway collapse, including weight loss, pharmacological management, upper airway reconstructive surgery, or continuous positive airway pressure (CPAP). CPAP at present is now the most favored method for treating OSA, being used in approximately 80% of all newly diagnosed cases of OSA. In spite of its current widespread use CPAP is still not the ideal treatment. For example less than half of CPAP patients use CPAP regularly. More conservative measures such as weight loss and pharmacological treatment have also met with minimal success due to compliance problems or the development of side effects. Surgical reconstruction of the upper airway (uvulopalatopharyngoplasty or UPPP) has also met with equivocal results, mostly due to an inability to select the optimal patient for this particular form of treatment.

Stimulation of the upper airway and in particular of the hypoglossal nerve in synchrony with the inspiratory phase of respiration is a further alternative therapy for patients with OSA. Patients treated with such a upper airway stimulation system are provided the opportunity to gain restful, uninterrupted sleep otherwise not possible due to the obstructive apnea episodes. At present such a system is available from Medtronic, Inc. The system for stimulation consists of an implanted programmable pulse generator, such as the Medtronic Inspire Model 3024 Implantable pulse generator, a stimulating lead, such as the Medtronic Model 3990 half cuff electrode, and a dP/dt pressure sensing lead to signal respiration, such as the Medtronic model 4322 pressure sensor. Preliminary results demonstrate that hypoglossal nerve stimulation for treatment of OSA is successful.

In spite of the initial success, stimulation synchronized with respiration is, in some patients, a problem due to cardiac artifact in the pressure signal. Although in some patients the pressure signal is only minimally affected by the cardiac artifact, resulting in excellent synchronized pacing, in other patients cardiac artifact makes detection of respiration less reliable.

FIGS. A and B illustrate the problem of cardiac artifacts in the pressure signal. FIG. A details the sensed pressure signal due to respiration. As seen in this embodiment, the sensed pressure signal is generally sinusoidal. As further seen in this figure, the bottom tracing shows the stimulus markers, positive spikes indicating stimulation begins while negative spikes indicate the stimulation stops.

FIG. B, in contrast, shows a pressure signal having an unacceptably large cardiac artifact. As seen, this type of pressure signal is much less rhythmic or repetitive as that shown above. As can be appreciated, this non-rhythmic signal makes the interpretation of the pressure signal much more difficult, if not impossible. Thus, when such a large degree of cardiac artifact is present a reliable and accurate sensing of pressure is inhibited, leading to a not optimally therapeutic delivery of stimulation, seen here as lower tracing in this figure.

Thoracic impedance measures is a widely accepted method of detection of respiration, the concept being a change in lung volume during respiration. However, during an obstruction of the upper airway, the lung volume hardly changes, making thoracic impedance measures unsuitable for detection of respiratory effort. Patients with obstructive sleep apnea still try to breathe and, therefore, lower the diaphragm. Therefore, impedance measures over the diaphragm should result in a signal related to respiratory effort. This signal can be used as an input signal for a hypoglossal nerve stimulator.

SUMMARY OF THE PRESENT INVENTION

The present invention provides obstructive sleep apnea treatment through stimulation to the hypoglossal nerve synchronized with respiratory effort. In the preferred embodiment such stimulation is provided by an implantable pulse generator, the implantable pulse generator having a stimulation stage to output stimulation pulses to a body structure, a sensing stage to sense the respiratory effort of a patient, and a controller, to coordinate, and preferably to synchronize, the output stimulation pulses with the sensed respiratory effort. In the preferred embodiment the respiratory effort of a patient is sensed through the use of two electrodes disposed such that the diaphragm is positioned between, and the high frequency alternating current is injected from one electrode to the other and the corresponding impedance is measured, the corresponding impedance thus being a function of the diaphragm position, itself indicating the respiratory effort of the patient. In such a manner the present invention permits the delivery of stimulation to be precisely controlled by the actual respiratory effort of the patient.

BRIEF DESCRIPTION OF THE DRAWINGS

FIGS. A and B illustrate the problem of cardiac artifacts in the pressure signal.

The Figures are not necessarily to scale.

DETAILED DESCRIPTION OF THE DRAWINGS

Figure 1:
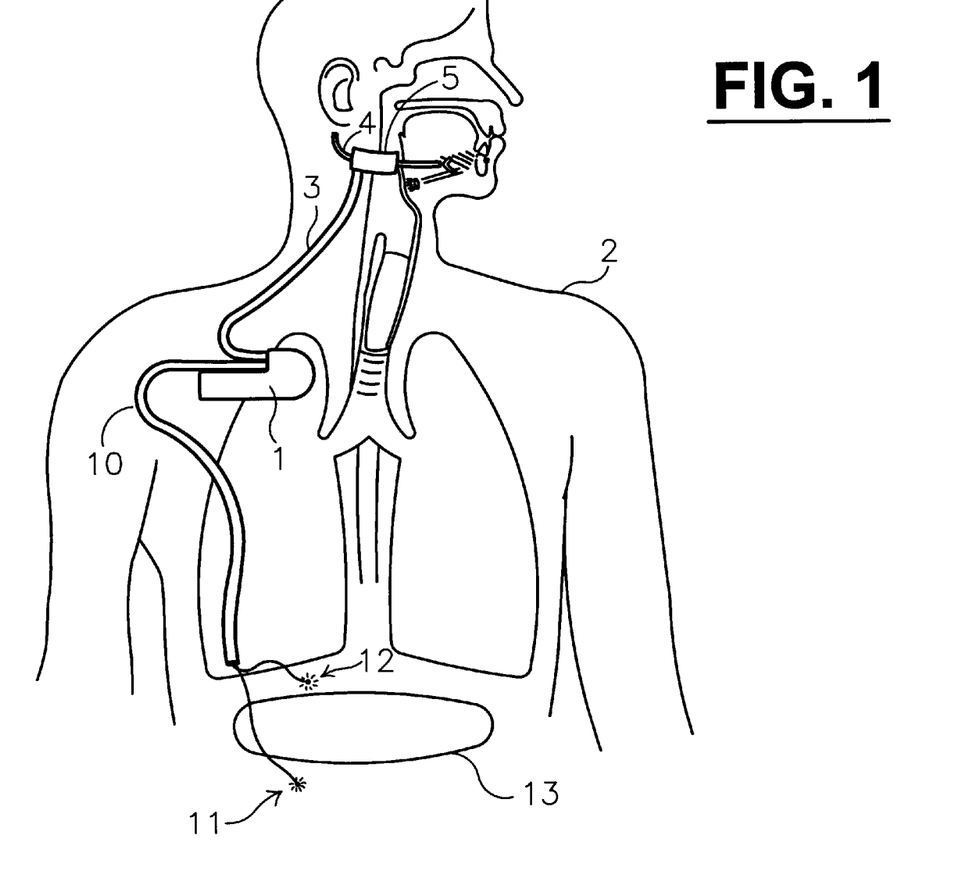
FIG. 1 shows the present invention implanted in a patient.

FIG. 1 shows the present invention implanted in a patient. As seen, device 1 is implanted in patient 2, preferably subcutaneously along the upper chest wall. Of course, the device may further be implanted in other areas and is only limited in its selected position by the desired length of the leads coupling the device to the relative body structures. Device has first lead 3 which couples the device to the hypoglossal nerve 4 through cuff portion 5 of lead 3. In the preferred embodiment lead 3 having cuff portion 5 is the Medtronic model 3990 half cuff nerve electrode. Of course, other leads may be used depending upon the preference of the physician and the particular anatomical constraints of the patient. An additional lead 10 is coupled to device 1. Lead 10 features a first electrode 11 and a second electrode 12. These electrodes are preferably positioned adjacent but not within diaphragm muscle 13. Electrodes are further preferably positioned such that they will not move during or along with movement of the diaphragm during respiration. In the preferred embodiment, electrodes 11 and 12 are positioned at the level of the lowermost rib in the ribcage by being sutured to the subcutaneous tissue. Of course, the electrodes may be positioned in other acceptable manners, such as even directly to the respective ribs using, e.g., sutures, staples, screws, glue, etc.

Figure 2A:
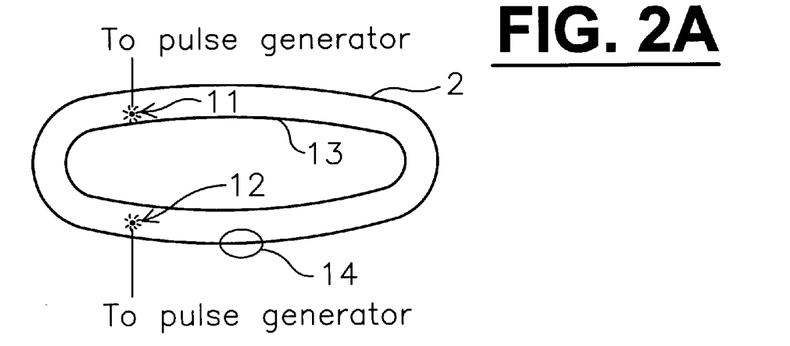
FIG. 2A is a sectional view of the patient shown in FIG. 1 detailing the disposition of the electrodes across the diaphragm.

FIG. 2 is a sectional view of the patient shown in FIG. 1 detailing the disposition of the electrodes across the diaphragm. As seen, electrode 11 is preferably positioned in the front or anterior while electrode 12 is preferably positioned in the back or posterior area of the thoracic cavity near spinal column 14. As discussed above, electrode may be mounted to any acceptable body structure in any manner acceptable, e.g. rib, tendon, etc. by, e.g., sutures, staples, screws, glue, etc. Moreover, any electrode design acceptable may be used.

Figure 2B:
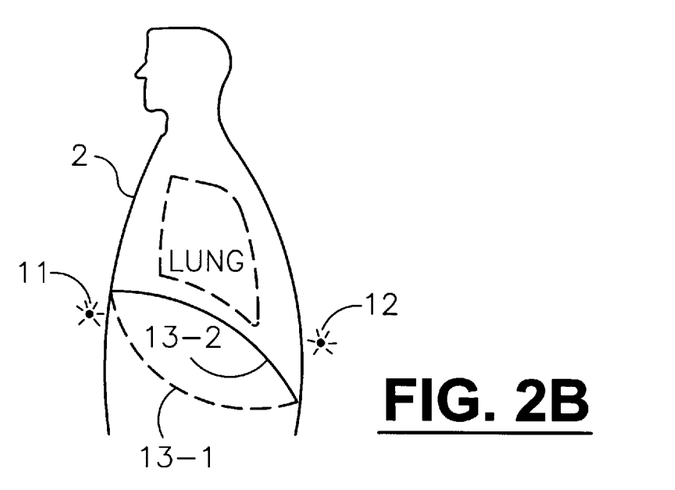
FIG. 2B is a cross-sectional view of the patient shown in FIG. 1 detailing the disposition of the electrodes across the diaphragm.

FIG. 2B is a cross-sectional view of the patient shown in FIG. 1 detailing the disposition of the electrodes across the diaphragm. This view especially shows the relative change in position of the diaphragm during inspiration and exhalation. As seen, during inspiration the diaphragm moves into a lower position, as designated by the dotted line 13-1. During exhalation the diaphragm moves upwardly into a higher position, as designated by the dotted line 13-2. As a result, the impedance of the tissue measured between electrodes 11 and 12 changes from low impedance at the end of expiration when mainly muscle, fat, and organ tissue is in between the electrodes 11 and 12, to high impedance during an attempt to inhale, when mainly lung tissue filled with air comes in between the electrodes.

Figure 3:
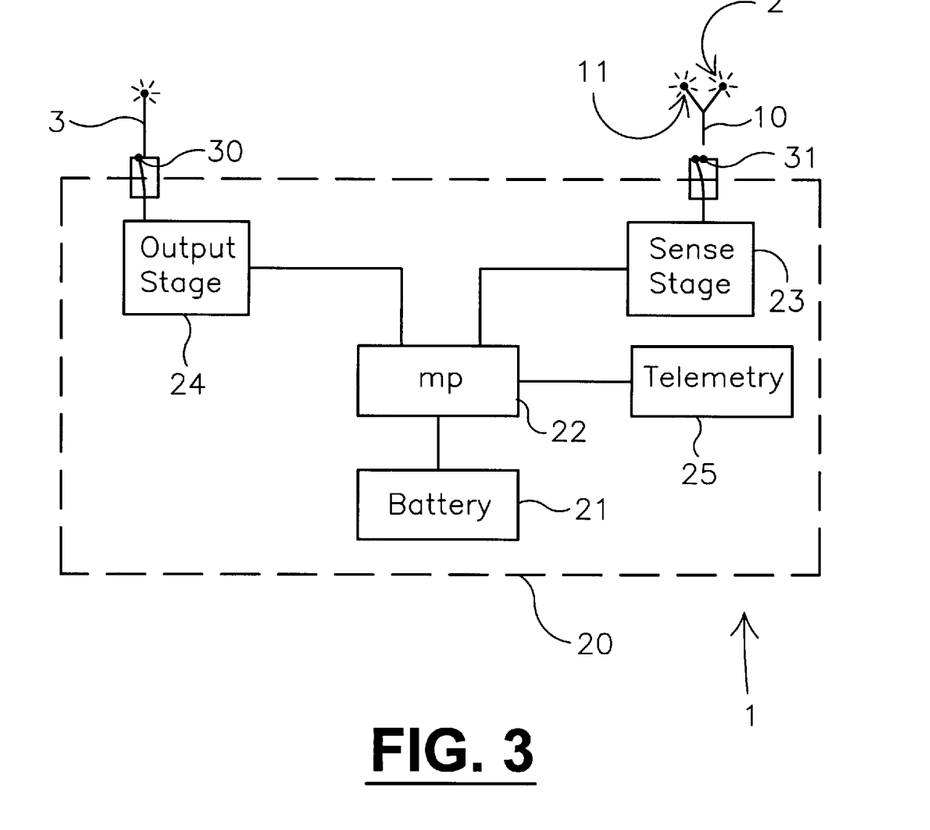
FIG. 3 is a block diagram of the present invention.

FIG. 3 is a block diagram of the present invention. As seen, device 1 is contained within a hermetic enclosure 20. Device is powered by battery 21 which is coupled to microprocessor 22 which, in turn, is coupled to the sense stage 23 as well as the output stage 24. Telemetry 25 is further provided to permit the device to be remotely accessed and controlled by the physician. Output stage outputs through one or more feedthroughs 30 to lead 3. Sense stage, likewise, is coupled through one or more feedthroughs 31 to lead 10 having electrodes 11 and 12. As discussed in more detail below, sense stage 23 includes a pulse generator and impedance sensing circuit, as is well known in the art. Such a device permits the sense stage to output a high frequency current through electrode 11 to be sensed by electrode 12. The measured impedance between electrodes 11 and 12 is thereafter used to sense the respiratory effort of the diaphragm. This information is thereafter processed by microprocessor and used to control output stage 24. Any acceptable or high frequency current may be delivered through electrode 11 to electrode 12 for sensing respiratory effort, such as a 1 mA AC current delivered with a frequency between 4 kHz–64 kHz, for example.

Figure 4:
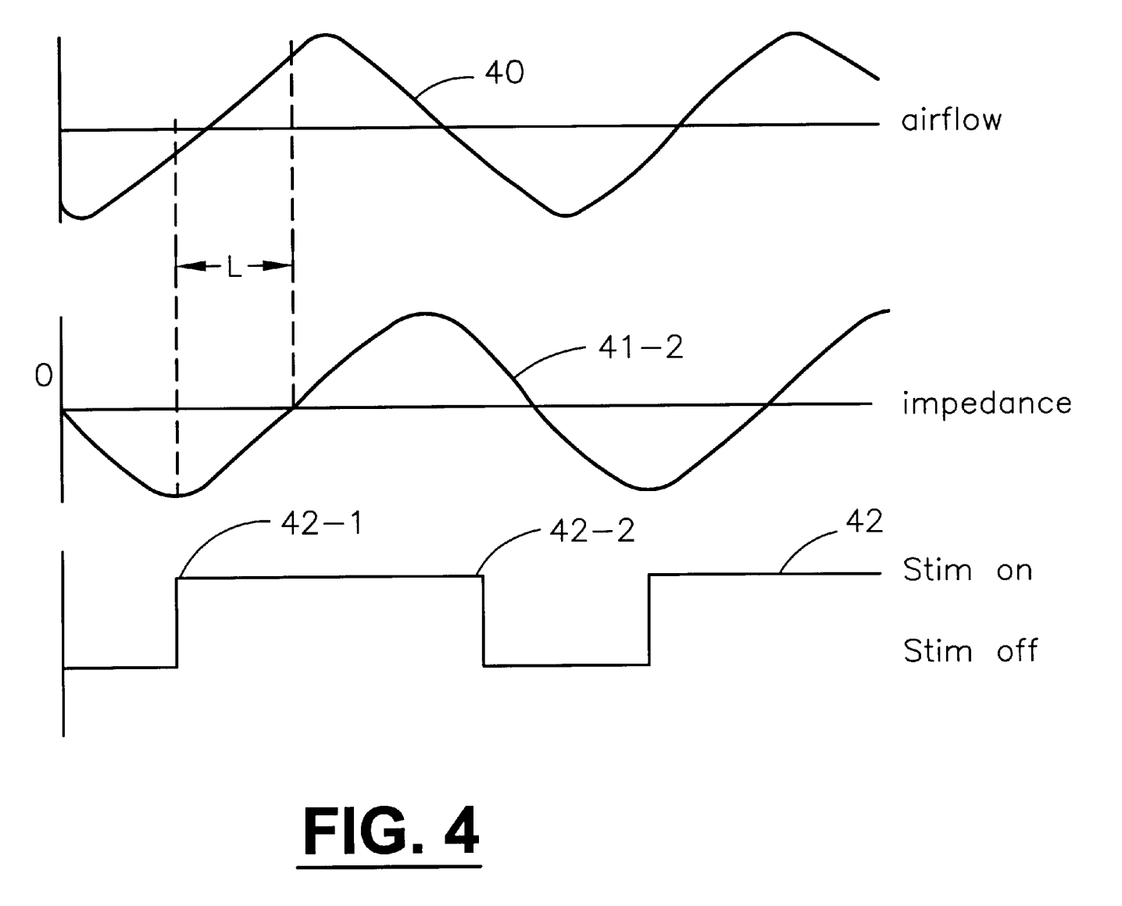
FIG. 4 shows a relationship between respiratory effort airflow and the delivery of stimulation as practiced in the present invention.

FIG. 4 shows a relationship between respiratory effort, airflow and the delivery of stimulation as practiced in the present invention. As seen, line 40 shows a typical airflow pattern for a respiratory cycle. As seen, the airflow essentially occurs in a sinusoidal wave pattern oscillating between the inhalation of air and the exhalation of air. To be precise, the maximum of air in occurs when the airflow signal crosses zero in a downwards direction, minimum airflow in is when the airflow signal crosses zero in an upwards direction. The oscillation is between maximum flow and minimum flow. Therefore, airflow starts (at zero) at inspiration shortly after a negative pressure occurs because of the fact that the diaphragm lowers: thus shortly after an increase of the impedance. Line 41 depicts the change in impedance as a result of alternating diaphragmatic muscle contraction/relaxation. The impedance is proportional to respiratory effort. When the impedance is minimal (diaphragm completely up) inspiration starts. When impedance crosses zero, the airflow reaches its maximum (or minimum during expiration). Thus the phase shift "L" is at least 90°. As seen, respiratory effort is basically synchronized to the airflow, although slightly leading or ahead of phase to the airflow, as seen by "L". This is not surprising as it is the respiratory effort which gives rise to the airflow. Line 42 shows the stimulation marker channel of the present device. In the preferred embodiment the stimulation is triggered by the impedance crossing a predetermined stimulation threshold, here shown as corresponding to the lowest sensed impedance. Of course, the predetermined stimulation threshold may be set to any acceptable manner and in the preferred embodiment would be completely programmable. As seen, when the sensed impedance crosses the predetermined stimulation threshold, depicted at 41-1, stimulation is triggered as represented at 42-1 on the stimulation marker channel line. Stimulation is thereafter provided to the hypoglossal nerve through lead 3 and cuff 5 as already discussed above. Stimulation may be provided for any amount of time, and in the preferred embodiment is turned off once a desired change in impedance is sensed. That is stimulation is turned off once the slope of the sensed impedance is negative and crosses a predetermined threshold. The maximum negative slope shown here is occurring at 41-2 and causing the corresponding cessation of stimulation at 42-2. Like the stimulation threshold, however, any desired parameters may be used or sensed to control the cessation of stimulation.

Figure 5A:
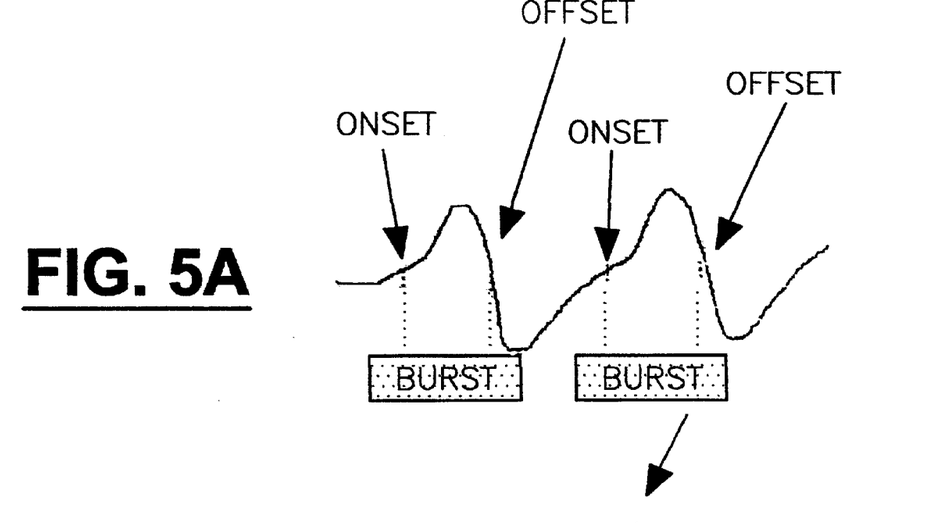
FIG. 5A shows a typical sensed intrathoracic pressure waveform and the corresponding areas during which stimulation is delivered.
Figure 5B:
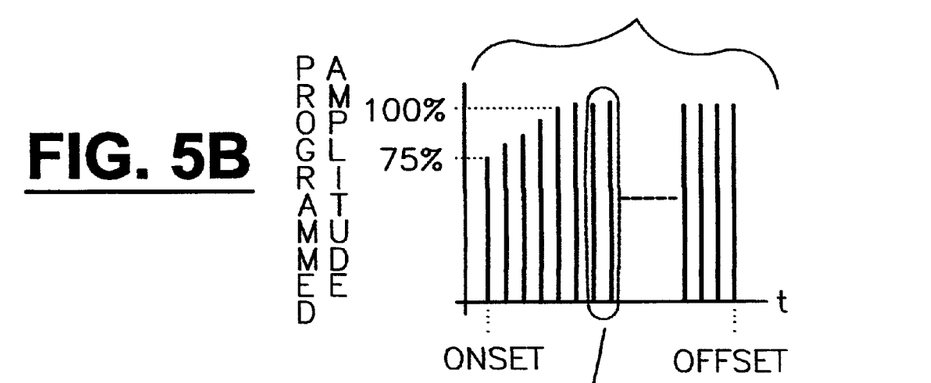
FIG. 5B shows the gradual ramping up in stimulation amplitude delivered to the nerve in the preferred embodiment.
Figure 5C:
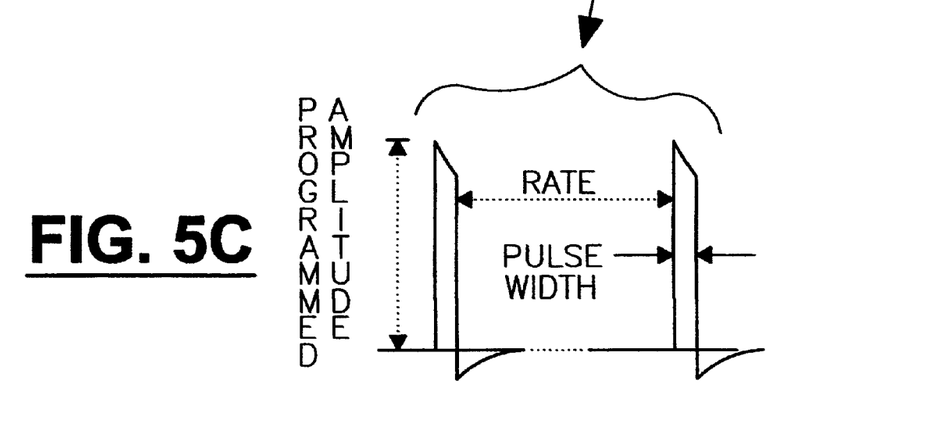
FIG. 5C depicts the preferred stimulation waveform.

FIG. 5A shows a typical sensed intrathoracic pressure waveform and the corresponding areas during which stimulation is delivered. Stimulation, for example could be turned off only as a function of time or as only a function of sensed impedance. FIG. 5B shows the gradual ramping up in stimulation amplitude delivered to the nerve in the preferred embodiment. The amplitude of each pulse train delivered is ramped up so as to have a gradual effect on the patient. FIG. 5C depicts the preferred stimulation waveform. The stimulation parameters, may be as follows: Voltage between approximately 0–10.5V; Rate between approximately 20–40 pps; and Pulse width between approximately 65–208 $\mu$-sec. These pulses are monophasic, but net charge is zero. A cuff electrode such as the Medtronic model 3990 A or B may be used. Preferably the cuff electrode features 3 electrodes, the outer 2 are positive (anode) and the middle is always negative (cathode).

Figure 6:
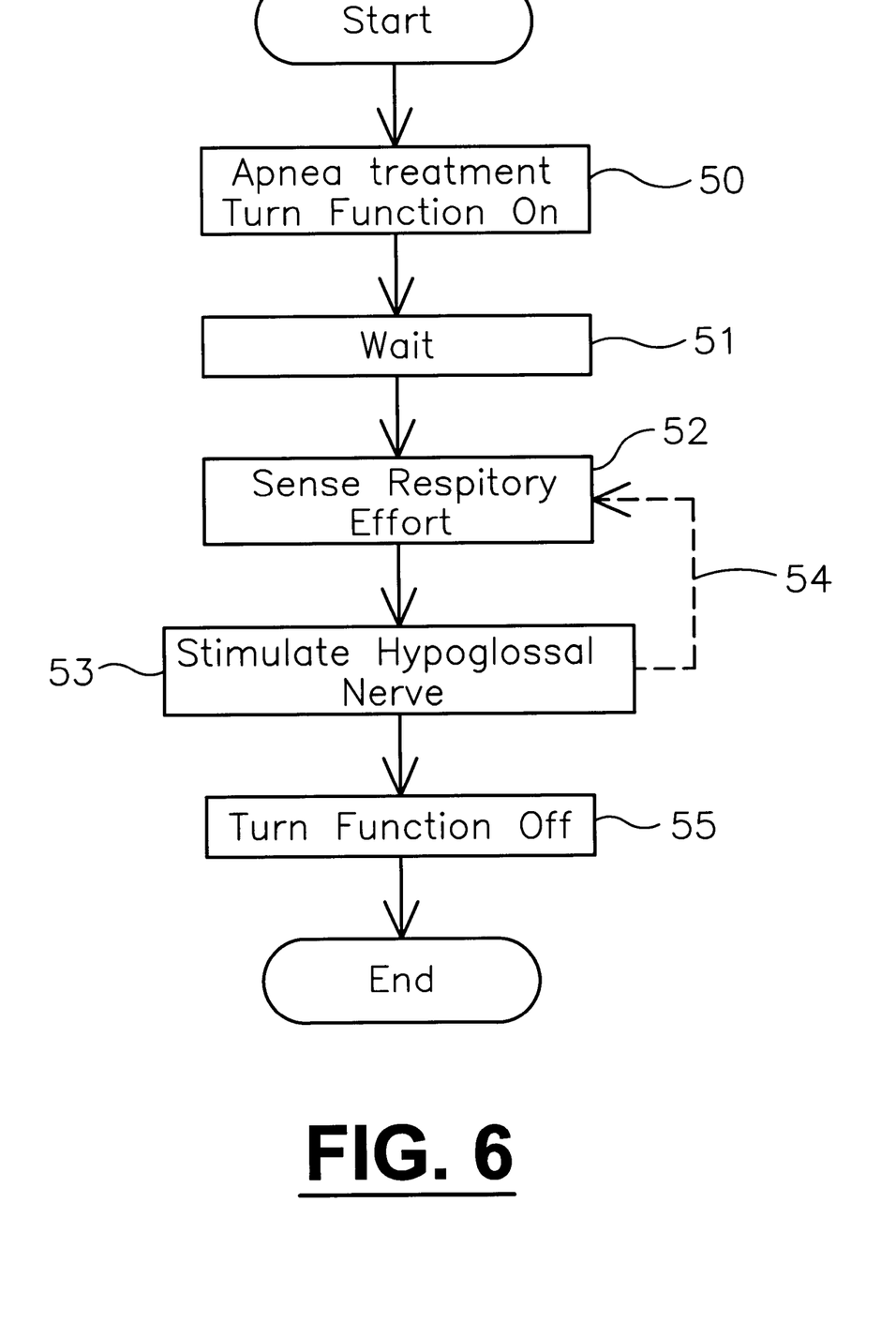
FIG. 6 is a flowchart detailing the operation of the present invention.

FIG. 6 is a flow chart detailing the operation of the present invention. As seen, operation of the device begins when apnea treatment function is turned on in block 50. Device may be turned on by the patient himself, such as using a programmer. Other methods may also be used, such as EEG sensing. Next, the device proceeds to block 51 and waits for a predetermined period of time. This permits the device to operate only once it is believed the patient is already asleep. As can be appreciated, the device's stimulation to the hypoglossal nerve causes the tongue to move forward and thus away from the air passage. If the patient were to sleep while such stimulation were being delivered, he may find difficulty attaining or entering into sleep and, therefore, in the preferred embodiment the device waits for a predetermined period (programmable) of time before beginning the treatment of apnea through the sensing of respiratory effort. It should be understood that the device may have other methods of ensuring that stimulation is only provided when the patient is asleep, such methods include an activity sensor, posture sensor, EEG sensor, temperature sensor, ECG sensor or any combinations thereof. What is important is that the stimulation is only provided when the patient is asleep and not in the period of time when the patient is trying to go to sleep. At 52 the device begins to sense respiratory effort. As discussed above, in this block high frequency current is injected across the diaphragm and the resulting impedance is sensed between two electrodes. Once respiratory effort has been sensed in block 52, the device proceeds to block 53 and provides stimulation to the hypoglossal nerve. The device would continue to both sense the respiratory effort and provide stimulation, as shown by dotted lime 54 until the apnea treatment function has been turned off in block 55. Thereafter treatment is ended and will not begin again until turned on. The device may be turned off in any number of acceptable manners, including 1) by the patient himself, using a patient programmer (not a magnet); 2) by a time-out option (therapy stops automatically when the device is on for a programmable number of hours—typically between 1 and 15 hours); and 3) there are programmable delay times—just like before falling asleep, when the patient wakes up in the night, he can restart the device: a new delay (programmable) will start.

Although hypoglossal nerve stimulation is disclosed it should be understood other nerves and structures may either or also be stimulated, including muscles, etc. Moreover, although electrodes implanted adjacent the diaphragm, they may also be implanted in other areas, such as abdominal, pectoral, etc.

Although various embodiments of the invention have been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. An implantable pulse generator for treating obstructive sleep apnea in a patient, comprising:

means for determining when the patient has entered a sleep state;

means for electrically stimulating a nerve in the upper airway tract of the patient to elicit a contraction by an innervated muscle, the means for electrically stimulating being operative for a pre-determined period of time after the sleep state determining means determines the patient has entered the sleep state;

means for sensing the respiratory effort of a patient comprising first and second electrodes suitable for placement on opposite sides of the patient's diaphragm, the respiratory effort sensing means delivering high frequency current between the electrodes to thereby measure the impedance therebetween; and a controller to control the means for electrically stimulating in coordination with the sensed respiratory effort.

2. The implantable pulse generator according to claim 1 wherein the means for electrically stimulating a nerve in the upper airway tract comprises means for delivery electrical stimulation pulse trains.

3. The implantable pulse generator according to claim 2 means for delivery electrical stimulation pulse trains comprises means for delivery the electrical stimulation pulse trains to a nerve.

4. The implantable pulse generator according to claim 3 wherein the controller controls the means for electrically stimulating in synchrony with the sensed respiratory effort of a patient such that the means for electrically stimulating is activated only upon a sensed respiratory effort of a patient.

5. The implantable pulse generator according to claim 1 wherein the means for sensing the respiratory effort of a patient comprise a first electrode adapted to be positioned adjacent the diaphragm and a second electrode adapted to be positioned adjacent the diaphragm and opposite the first electrode, such that the diaphragm can be disposed between the first and second electrodes.

6. The implantable pulse generator according to claim 5 further comprising means for and sensing the impedance between the first electrode and the second electrode.

7. The implantable pulse generator according to claim 6 wherein the means for and sensing the impedance between the first electrode and the second electrode further comprises means for injecting a high frequency current between the first electrode and the second electrode.

8. The implantable pulse generator according to claim 7 wherein the means for injecting a high frequency current between the first electrode and the second electrode comprises means for injecting an alternating current having an amplitude of approximately 1 mAmp and a frequency between approximately 4 kHz–64 kHz.

9. The implantable pulse generator according to claim 1 wherein the controller controls the means for electrically stimulating in synchrony with the sensed respiratory effort of a patient.

10. A method of treating obstructive sleep apnea in a patient, comprising the steps of:

determining when the patient has entered a sleep state;

sensing respiratory effort of the patient using first and second electrodes disposed on opposite sides of the patient's diaphragm, the first and second electrodes delivering high frequency current thereacross to permit measurement of the impedance therebetween as a measure of the sensed respiratory effort; and continuously stimulating a hypoglossal nerve of the patient for a pre-determined period of time after the sleep state has been entered, the stimulation being provided in coordination with the sensed respiratory effort.

11. The method of claim 10 wherein the step of sensing the respiratory effort further comprises injecting high frequency current across the diaphragm and sensing the resulting impedance.

12. The method of claim 11 wherein the step of injecting high frequency current across the diaphragm comprises injecting an alternating current having an amplitude of approximately 1 mAmp and a frequency between approximately 4 kHz–64 kHz.

13. The method of claim 10 wherein the step of stimulating the hypoglossal nerve comprises delivering electrical stimulation pulse train to the hypoglossal nerve.

14. The method of claim 13 wherein the step of delivering electrical stimulation pulse train to the hypoglossal nerve comprises delivering a series of at least two pulse to the hypoglossal nerve.

15. The method of claim 14 wherein the step of delivering electrical stimulation pulse train to the hypoglossal nerve comprises delivering a series of at least two pulse monophasic pulses to the hypoglossal nerve.

16. The method of claim 15 wherein the step of delivering electrical stimulation pulse train to the hypoglossal nerve comprises delivering a series of at least two pulse having an amplitude of between approximately 1–50 milliamps and pulse width between approximately 3–1000 microseconds.

* * * * *